US008008419B2

(12) United States Patent
Dershem

(10) Patent No.: US 8,008,419 B2
(45) Date of Patent: Aug. 30, 2011

(54) SILOXANE MONOMERS AND METHODS FOR USE THEREOF

(75) Inventor: Stephen M. Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 30 days.

(21) Appl. No.: 12/541,027

(22) Filed: Aug. 13, 2009

(65) Prior Publication Data

US 2010/0041823 A1 Feb. 18, 2010

Related U.S. Application Data

(60) Provisional application No. 61/088,612, filed on Aug. 13, 2008.

(51) Int. Cl.
C08F 30/08 (2006.01)
C07F 7/08 (2006.01)
(52) U.S. Cl. .......... 528/31; 526/279; 526/319; 526/332; 526/346; 528/26; 556/445; 556/460; 556/479
(58) Field of Classification Search .................. None
See application file for complete search history.

(56) References Cited

U.S. PATENT DOCUMENTS

| | | | |
|---|---|---|---|
| 3,336,266 A | 8/1967 | McConnell et al. | |
| 3,739,041 A | 6/1973 | Schmid et al. | |
| 4,937,017 A * | 6/1990 | Gillberg-LaForce et al. | 252/582 |
| 4,944,989 A | 7/1990 | Dorsch et al. | |
| 4,968,738 A | 11/1990 | Dershem | |
| 5,045,127 A | 9/1991 | Dershem et al. | |
| 5,064,480 A | 11/1991 | Dershem et al. | |
| 5,232,962 A | 8/1993 | Dershem et al. | |
| 5,306,333 A | 4/1994 | Dershem et al. | |
| 5,358,992 A | 10/1994 | Dershem et al. | |
| 5,378,790 A | 1/1995 | Michalczyk et al. | |
| 5,403,389 A | 4/1995 | Dershem | |
| 5,447,988 A | 9/1995 | Dershem et al. | |
| 5,489,641 A | 2/1996 | Dershem | |
| 5,539,137 A * | 7/1996 | Lewis et al. ............. | 556/450 |
| 5,646,241 A | 7/1997 | Dershem et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,760,165 A | 6/1998 | Dao et al. | |
| 5,861,111 A | 1/1999 | Dershem et al. | |
| 5,969,036 A | 10/1999 | Dershem | |
| 5,973,166 A | 10/1999 | Mizori et al. | |
| 6,034,150 A | 3/2000 | Hoyle et al. | |
| 6,034,194 A | 3/2000 | Dershem | |
| 6,034,195 A | 3/2000 | Dershem | |
| 6,063,828 A | 5/2000 | Ma et al. | |
| 6,121,358 A | 9/2000 | Dershem et al. | |
| 6,187,886 B1 | 2/2001 | Husson et al. | |
| 6,211,320 B1 | 4/2001 | Dershem et al. | |
| 6,265,530 B1 | 7/2001 | Herr et al. | |
| 6,281,314 B1 | 8/2001 | Tong | |
| 6,300,456 B1 | 10/2001 | Musa | |
| 6,316,566 B1 | 11/2001 | Ma et al. | |
| 6,355,750 B1 | 3/2002 | Herr | |
| 6,369,124 B1 | 4/2002 | Hoyle et al. | |
| 6,423,780 B1 | 7/2002 | Dershem et al. | |
| 6,429,281 B1 | 8/2002 | Dershem et al. | |
| 6,451,929 B1 | 9/2002 | Smits et al. | |
| 6,482,899 B2 | 11/2002 | Ohashi et al. | |
| 6,521,731 B2 | 2/2003 | Dershem et al. | |
| 6,620,946 B2 | 9/2003 | Dershem et al. | |
| 6,743,852 B2 | 6/2004 | Dershem et al. | |
| 6,750,301 B1 | 6/2004 | Bonneau et al. | |
| 6,790,597 B2 | 9/2004 | Dershem | |
| 6,825,245 B2 | 11/2004 | Dershem | |
| 6,831,132 B2 | 12/2004 | Liu et al. | |
| 6,852,814 B2 | 2/2005 | Dershem et al. | |
| 6,855,745 B2 | 2/2005 | Hoyle et al. | |
| 6,916,856 B2 | 7/2005 | Dershem | |
| 6,946,523 B2 | 9/2005 | Dershem et al. | |
| 6,960,636 B2 | 11/2005 | Dershem et al. | |
| 6,963,001 B2 | 11/2005 | Dershem et al. | |
| 7,102,015 B2 | 9/2006 | Dershem et al. | |
| 7,157,587 B2 | 1/2007 | Mizori et al. | |

(Continued)

FOREIGN PATENT DOCUMENTS

CN 1187507 A 7/1998

(Continued)

OTHER PUBLICATIONS

"Highly Stereoselective Synthesis and Application of Functionalized Tetravinylcyclotetrasiloxanes via Catalytic Reaction" authored by Marciniec et al. and published in the Journal of Molecular Catalysis A: Chemical (2007) 265, 25-31.*
"A Novel Organometallic Route to Phenylethenyl-modified Polysiloxanes" authored by Ganicz et al., and published in J. Mater. Chem. (2205) 15, 611-619.*
Machine translation of JP 2003-128765 A.*
Adamson "Review of CSP and Flip Chip Underfill Processes and When to Use the Right Dispensing Tools for Efficient Manufacturing", *Paper Presented at GlobalTRONICS Technology Conference*, Singapore 2002, 1-6.
Andersson et al., "Initiator-Free Photopolymerization of an Aliphatic Vinyl Ether-Maleimide Monomer", *J Coatings Tech 69* 1997, 91-95.
Fouassier "Photoinitiation, Photopolymerization, and Photocuring", *Hanser/Gardner* 1995, 276-283.
Kohli et al., "Co-Polymerization of Maleimides and Vinyl Ethers: A Structural Study", *Macromolecules 31*: 1998, 5681-5689.
Krishnan et al., "Synthesis, Characterization, and Curing Kinetics of Novel Ladder-Like Polysilsesquioxanes Containing Side-Chain Maleimide Groups", *Journal of Polymer Science: Part A: Polymer Chemistry*. vol. 42: 2004, 4036-4016.

(Continued)

*Primary Examiner* — Marc S Zimmer

(74) *Attorney, Agent, or Firm* — The Law Office of Jane K. Babin, Professional Corporation; Jane K. Babin

(57) ABSTRACT

The invention provides novel siloxane monomers useful in a variety of adhesive applications. In one aspect, the siloxane compounds described herein can be used as Diels-Alder type curatives for bismaleimide or poly-maleimide monomers. The unsaturated resins shown here are attractive for use as maleimide curatives due to their poly-functionality. Each substituted styrenyl residue can react with two maleimide functional groups. Thus, an invention adhesive composition typically contains an excess of bismaleimide monomers.

19 Claims, No Drawings

U.S. PATENT DOCUMENTS

| | | |
|---|---|---|
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,326,754 B2 | 2/2008 | Nikolic et al. |
| 7,517,925 B2 | 4/2009 | Dershem et al. |
| 7,678,879 B2 | 3/2010 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0129438 A1 | 7/2003 | Becker et al. |
| 2003/0148226 A1 | 8/2003 | Kodama et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0054143 A1* | 3/2005 | Skokov et al. ............... 438/123 |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0137340 A1 | 6/2005 | Nikolic et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0030672 A1 | 2/2006 | Nikolic et al. |
| 2006/0063014 A1 | 3/2006 | Forray |
| 2006/0069232 A1 | 3/2006 | Dershem |
| 2006/0142517 A1 | 6/2006 | Dershem |
| 2006/0183846 A1 | 8/2006 | Pfenninger et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | |
|---|---|---|
| EP | 1156034 | 11/2001 |
| EP | 1156036 | 11/2001 |
| EP | 1834969 | 9/2007 |
| JP | 05345880 | 12/1993 |
| JP | 10287715 | 10/1998 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

OTHER PUBLICATIONS

* cited by examiner

SILOXANE MONOMERS AND METHODS FOR USE THEREOF

RELATED APPLICATIONS

This application claims the benefit of priority under 35 USC §119 of U.S. Provisional Application Ser. No. 61/088,612 filed Aug. 13, 2008, the entire disclosure of which is incorporated herein by reference.

FIELD OF THE INVENTION

The present invention relates to thermosetting adhesive compositions, methods of preparation and uses therefor. In particular, the present invention relates to thermosetting compositions containing olefinic and/or epoxy functional siloxane monomers.

SUMMARY OF THE INVENTION

The present invention provides novel linear and cyclic siloxane monomers useful in a variety of applications, such as adhesive applications. The siloxane compounds have a structure represented by formula I:

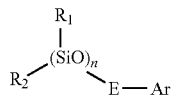

Where $R_1$ is selected from the group consisting of $C_1$ to $C_{10}$ alkyls; $R_2$ is absent or is selected from the group consisting of $C_1$ to $C_{10}$ alkyls; E is selected from the group consisting of an alkenylene and oxiranylene; Ar is a substituted or an unsubstituted aryl; and n is an integer having the value between 1 and 20, with the further proviso that the compound is a cyclic siloxane or a linear siloxane.

In certain embodiments the compound is a cyclic siloxane, $R_2$ is absent, and n has the value between 3 and 6. In other embodiments, $R_1$ is a $C_1$ to about $C_5$ alkyl. In certain aspects, $R_1$ is methyl. In yet further embodiments $R_1$ is selected from $C_2$ to about $C_{10}$ alkyls.

In some aspects of the invention E is $C_2$ alkenylene. The substituted or unsubstituted aryl of formula I, can be for example, a $C_6$ aryl. Among the substituents the aryl can substituted with are an alkyl, an alkenyl, an alkynyl, hydroxy, oxo, an alkoxy, mercapto, an unsubstituted cycloalkyl, a substituted cycloalkyl, an unsubstituted heterocyclic moiety, a substituted heterocyclic moiety, an unsubstituted aryl, a substituted aryl, an unsubstituted heteroaryl, a substituted heteroaryl, an unsubstituted aryloxy, a substituted aryloxy, a halogen, a haloalkyl, cyano, nitro, nitrone, amino, amido, —C(O)H, —C(O)—, —OC(O)—, —(O)CO—, —S—, —S(O)$_2$—, —OC(O)—O—, —NR'—C(O)—, —NR'—C(O)—NR'—, and —OC(O)—NR'—, wherein R' is selected from the group consisting of H, a lower alkyl, an acyl, an oxyacyl, carboxyl, carbamate, sulfonyl, sulfonamide, and sulfuryl.

Exemplary compounds of formula I provided by the invention include compounds 1, 2, and 3, described herein below.

Also provided by the invention are compositions comprising a compound of formula I. The compositions can be, for example, adhesive compositions, such as underfills, which can optionally include a fluxing agent and a filler. Adhesive compositions encompassed by the invention included both cured and uncured forms and may include one or more co-monomer selected from an acrylate, a methacrylate, a maleimides, a vinyl ether, a vinyl ester, styrenics and an allyl functional compound. The compositions provided by the invention also include other types of useful compositions, such as a coating In certain aspects, the invention provides linear siloxane compounds having the structure of formula II:

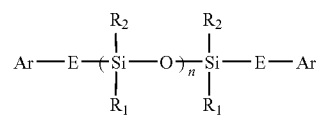

where each of $R_1$ and $R_2$ is independently selected from the group consisting of $C_1$ to $C_{10}$ alkyls, and n is 1 to 20.

An exemplary compounds according to formula II has the structure 4, described herein below. Additional exemplary compounds of the invention include compounds 5, 6, 7, and 8, described herein below.

The present invention also provides methods for increasing the adhesiveness of a composition comprising a monomer, by replacing all or a portion of the monomer in the composition with a compound of formula I or formula II. Such compositions can be, for example, adhesive compositions, such as an underfill. In some embodiments the monomer is a bismaleimide or poly-maleimide. Replacing all or a portion of the monomer according to this method increases the adhesiveness of the composition by about 2 fold in some embodiments.

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and Theological properties compatible with application to microelectronic and semiconductor components.

The demand for smaller and more powerful electronic components presents certain challenges to the microelectronic packaging industry. One way to include more semiconductor die in a component without increasing circuit board area is to arrange the die in a stacked configuration. Indeed, "stacked die" packages conserve "circuit board real estate" without sacrificing power or performance of the electronic component. In addition, the die used in stacked die applications are becoming ever thinner, requiring new adhesive solutions in order to preserve the integrity of these very thin die.

Moreover, other configurations of computer chips on circuit board such as those that require direct attachment to a substrate or board (e.g. "Flip Chips"), required similar properties to achieve higher speed and chip density on circuit boards. Yet with high density and direct contact between circuit boards and chips, there is concern about the thermomechanical expansion mismatch between the chip and the substrate or board, as well as concern that moisture can cause problems with tiny solder joints.

Thus, the microelectronics industry continues to require new adhesives that are able to meet its varying demands. Accordingly, there is a need for the development of materials to address the requirements of this rapidly evolving industry.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art, such as those set forth in "IUPAC Compendium of Chemical Terminology: IUPAC Recommendations (The Gold Book)" (McNaught ed.; International Union of Pure and Applied Chemistry, $2^{nd}$ Ed., 1997) and "Compendium of Polymer Terminology and Nomenclature: IUPAC Recommendations 2008" (Jones et al., eds; International Union of Pure and Applied Chemistry, 2009). Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms (although the term "alkyl" also includes instances where no numerical range of carbon atoms is designated).

"Adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the original individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures obtained from reactive curable original compound(s) or mixture(s) thereof which have undergone a chemical and/or physical changes such that the original compound(s) or mixture(s) is(are) transformed into a solid, substantially non-flowing material. A typical curing process may involve crosslinking.

"Curable" means that an original compound(s) or composition material(s) can be transformed into a solid, substantially non-flowing material by means of chemical reaction, crosslinking, radiation crosslinking, or the like. Thus, adhesive compositions of the invention are curable, but unless otherwise specified, the original compound(s) or composition material(s) is(are) not cured.

"Thermoplastic," as used herein, refers to the ability of a compound, composition or other material (e.g. a plastic) to dissolve in a suitable solvent or to melt to a liquid when heated and freeze to a solid, often brittle and glassy, state when cooled sufficiently.

"Thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° Celsius), via a chemical reaction (e.g. epoxy ring opening, free-radical polymerization, etc.), or through irradiation (e.g. visible light, U.V., or X-ray irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more oligomer or longer polymer chains by bridges of an element, a molecular group, a compound, or another oligomer or polymer. Crosslinking may take place upon heating; some crosslinking processes may also occur at room temperature or a lower temperature. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allows for low lamination temperatures while providing high thermal stability.

A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

"Underfill," "underfill composition" and "underfill material" are used interchangeably to refer to a material, typically polymeric compositions, used to fill gaps between a semiconductor component, such as a semiconductor die, and a substrate. "Underfilling" refers to the process of applying an underfill composition to a semiconductor component-substrate interface, thereby filling the gaps between the component and the substrate.

The term "monomer" refers to a molecule that can undergo polymerization or copolymerization thereby contributing constitutional units to the essential structure of a macromolecule (a polymer).

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

alternating copolymers, which contain regularly alternating monomer residues;

periodic copolymers, which have monomer residue types arranged in a repeating sequence;

random copolymers, which have a random sequence of monomer residue types;

statistical copolymers, which have monomer residues arranged according to a known statistical rule; and block copolymers, which have two or more homopolymer subunits linked by covalent bonds. The blocks of homopolymer within block copolymers, for example, can be of any length and can be blocks of uniform or variable length. Block copolymers with two or three distinct blocks are called diblock copolymers and triblock copolymers, respectively.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

As used herein, "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

As used herein, "aliphatic" refers to any alkyl, alkenyl, cycloalkyl, or cycloalkenyl moiety.

"Aromatic hydrocarbon" or "aromatic" as used herein, refers to compounds having one or more benzene rings.

"Alkane," as used herein, refers to saturated straight-chain, branched or cyclic hydrocarbons having only single bonds. Alkanes have general formula $C_nH_{2n+2}$. "Cycloalkane," refers to an alkane having one or more rings in its structure.

As used herein, "alkyl" refers to straight or branched chain hydrocarbyl groups having from 1 up to about 500 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups.

For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

"Substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl (e.g., aryl$C_{1-10}$alkyl or aryl$C_{1-10}$alkyloxy), heteroaryl, substituted heteroaryl (e.g., heteroaryl$C_{1-10}$ alkyl), aryloxy, substituted aryloxy, halogen, haloalkyl (e.g., trihalomethyl), cyano, nitro, nitrone, amino, amido, carbamoyl, =O, =CH—, —C(O)H, —C(O)O—, —C(O)—, —S—, —S(O)$_2$—, —OC(O)—O—, —NR—C(O)—, —NR—C(O)—NR—, —OC(O)—NR—, where R is H or lower alkyl, acyl, oxyacyl, carboxyl, carbamate, sulfonyl, sulfonamide, sulfuryl, $C_{1-10}$alkylthio, aryl$C_{1-10}$alkylthio, $C_{1-10}$alkylamino, aryl$C_{1-10}$alkylamino, N-aryl-N—$C_{1-10}$ alkylamino, $C_{1-10}$alkyl carbonyl, aryl$C_{1-10}$alkylcarbonyl, $C_{1-10}$alkylcarboxy, aryl $C_{1-10}$alkylcarboxy, $C_{1-10}$alkyl carbonylamino, aryl $C_{1-10}$alkylcarbonylamino, tetrahydrofuryl, morpholinyl, piperazinyl, and hydroxypyronyl.

As used herein, "cycloalkyl" refers to cyclic ring-containing groups containing in the range of about 3 up to about 20 carbon atoms, typically 3 to about 15 carbon atoms. In certain embodiments, cycloalkyl groups have in the range of about 4 up to about 12 carbon atoms, and in yet further embodiments, cycloalkyl groups have in the range of about 5 up to about 8 carbon atoms. and "substituted cycloalkyl" refers to cycloalkyl groups further bearing one or more substituents as set forth below.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl $C_{1-10}$alkyloxy$C_{1-10}$alkyl, $C_{1-10}$alkylthio$C_{1-10}$alkyl, aryl$C_{1-10}$ alkylthio$C_{1-10}$alkyl, $C_{1-10}$alkylamino$C_{1-10}$alkyl, aryl$C_{1-10}$ alkylamino$C_{1-10}$alkyl, N-aryl-N—$C_{1-10}$alkylamino$C_{1-10}$ alkyl, $C_{1-10}$alkylcarbonyl$C_{1-10}$alkyl, aryl $C_{1-10}$alkylcarbonyl $C_{1-10}$alkyl, $C_{1-10}$-alkylcarboxy$C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino$C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, "arylene" refers to a divalent aryl moiety. "Substituted arylene" refers to arylene moieties bearing one or more substituents as set forth above.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below. Some examples of included but are not limited to (4-hydroxyphenyl)ethyl, or (2-aminonaphthyl)hexenyl.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "hetero" refers to groups or moieties containing one or more heteroatoms such as N, O, Si and S. Thus, for example "heterocyclic" refers to cyclic (i.e., ring-containing) groups having e.g. N, O, Si or S as part of the ring structure, and having in the range of 3 up to 14 carbon atoms. "Heteroaryl" and "heteroalkyl" moieties are aryl and alkyl groups, respectively, containing e.g. N, O, Si or S as part of their structure. The terms "heteroaryl", "heterocycle" or "heterocyclic" refer to a monovalent unsaturated group having a single ring or multiple condensed rings, from 1 to 8 carbon atoms and from 1 to 4 hetero atoms selected from nitrogen, sulfur or oxygen within the ring.

The definition of heteroaryl includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl. 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N.sub.6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like. Furthermore, the term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

Hetero-containing groups may also be substituted. For example, "substituted heterocyclic" refers to a ring-containing group having in the range of 3 up to 14 carbon atoms that contains one or more heteroatoms and also bears one or more substituents, as set forth above. Examples of substituents include, but are not limited to halo, —OH, —SH, —CN, —NO$_2$, trihalomethyl, hydroxypyronyl, $C_{1-10}$alkyl, aryl$C_{1-10}$ alkyl, $C_{1-10}$alkyloxy$C_{1-10}$alkyl, aryl$C_{1-10}$alkyloxy $C_{1-10}$alkyl, $C_{1-10}$alkylthio$C_{1-10}$alkyl, aryl$C_{1-10}$alkylthio$C_{1-10}$ alkyl, $C_{1-10}$alkylamino$C_{1-10}$alkyl, aryl$C_{1-10}$alkylamino $C_{1-10}$alkyl, N-aryl-N—$C_{1-10}$alkylamino$C_{1-10}$alkyl, $C_{1-10}$alkylcarbonyl$C_{1-10}$alkyl, aryl$C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl $C_{1-10}$alkylcarbonylamino$C_{1-10}$alkyl, and aryl$C_{1-10}$alkylcarbonylamino $C_{1-10}$alkyl.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, "alkenyl," "alkene" or "olefin" refers to straight or branched chain unsaturated hydrocarbyl groups having at least one carbon-carbon double bond, and having in the range of about 2 up to 500 carbon atoms. In certain embodiments, alkenyl groups have in the range of about 5 up to about 250 carbon atoms, 5 up to about 100 carbon atoms, 5 up to about 50 carbon atoms or 5 up to about 25 carbon atoms. In other embodiments, alkenyl groups have in the range of about 6 up to about 500 carbon atoms, 8 up to about 500 carbon atoms, 10 up to about 500 carbon atoms or 20 up to about 500 carbon atoms or 50 up to about 500 carbon atoms.

In yet further embodiments, alkenyl groups have in the range of about 6 up to about 100 carbon atoms, 10 up to about 100 carbon atoms, 20 up to about 100 carbon atoms or 50 up to about 100 carbon atoms, while in other embodiments, alkenyl groups have in the range of about 6 up to about 50 carbon atoms, 6 up to about 25 carbon atoms, 10 up to about 50 carbon atoms, or 10 up to about 25 carbon atoms. "Substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene ($CH_2$) unit. "Substituted alkylene" and "substituted oxyalkylene" refer to alkylene and oxyalkylene groups further bearing one or more substituents as set forth above.

As used herein, "alkynyl" refers to straight or branched chain hydrocarbyl groups having at least one carbon-carbon triple bond, and having in the range of 2 up to about 100 carbon atoms, and "substituted alkynyl" refers to alkynyl groups further bearing one or more substituents as set forth below.

As used herein, "arylene" refers to a divalent aryl moiety. "Substituted arylene" refers to arylene moieties bearing one or more substituents as set forth above.

As used herein, "acyl" refers to alkyl-carbonyl species.

"Allyl" as used herein, refers to refers to a compound bearing at least one moiety having the structure:

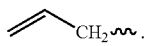

"Imide" as used herein, refers to a functional group having two carbonyl groups bound to a primary amine or ammonia. The general formula of an imide of the invention is:

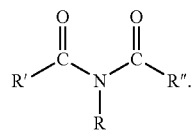

"Polyimides" are polymers of imide-containing monomers. Polyimides are typically linear or cyclic. Non-limiting examples of linear and cyclic (e.g. an aromatic heterocyclic polyimide) polyimides are shown below for illustrative purposes.

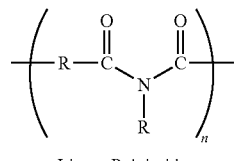

Linear Polyimide

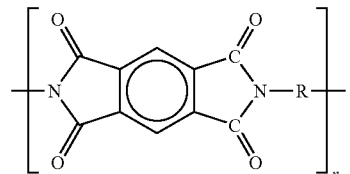

Aromatic Heterocyclic Polyimide

"Maleimide," as used herein, refers to an N-substituted maleimide having the formula as shown below:

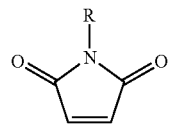

where R is an aromatic, herteroaromatic, aliphatic, or polymeric moiety.

"Bismaleimide" or "BMI", as used herein, refers to a polyimide having the general structure shown below:

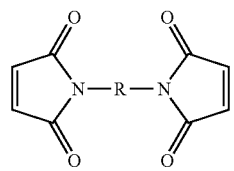

where R is an aromatic, herteroaromatic, aliphatic, or polymeric moiety.

BMIs can cure through an addition rather than a condensation reaction, thus avoiding problems resulting from the formation of volatiles. BMIs can be produced by a vinyl-type polymerization of a pre-polymer terminated with two maleimide groups.

As used herein, the term "acrylate" refers to a compound bearing at least one moiety having the structure:

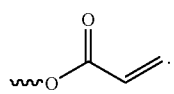

As used herein, the term "acrylamide" refers to a compound bearing at least one moiety having the structure:

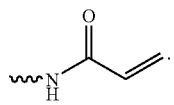

As used herein, the term "methacrylate" refers to a compound bearing at least one moiety having the structure:

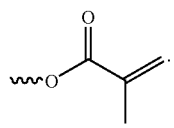

As used herein, the term "methacrylamide" refers to a compound bearing at least one moiety having the structure:

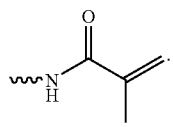

As used herein, the term "citraconimide" refers to a compound bearing at least one moiety having the structure:

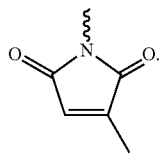

"Itaconate", as used herein refers to a compound bearing at least one moiety having the structure:

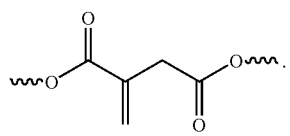

As used herein, the terms "halogen," "halide," or "halo" include fluorine, chlorine, bromine, and iodine.

As used herein, "siloxane" refers to any compound containing a Si—O moiety. The terms is inclusive of both linear and cyclic siloxanes. In certain embodiments, siloxanes of the invention include 2 or more repeating units of Si—O. Exemplary cyclic siloxanes include hexamethylcyclotrisiloxane, octamethylcyclotetrasiloxane, decamethylcyclopentasiloxane, dodecamethylcyclohexasiloxane and the like.

As used herein, "oxiranylene" or "epoxy" refers to divalent moieties having the structure:

The term "epoxy" is further used in conjunction with a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

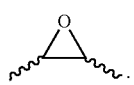

As used herein, the term "oxetane" refers to a compound bearing at least one moiety having the structure:

As used herein, the term "vinyl ether" refers to a compound bearing at least one moiety having the structure:

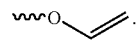

As used herein, the term "vinyl ester" refers to a compound bearing at least one moiety having the structure:

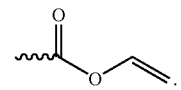

As used herein, "styrenic" refers to a compound bearing at least one moiety having the structure:

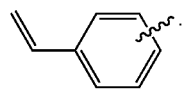

"Oxazoline" as used herein, refers to a compound bearing at least one moiety having the structure:

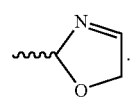

"Benzoxazine" as used herein, refers to a compound bearing at least one moiety having the structure:

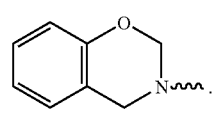

"Fumarate" as used herein, refers to a compound bearing at least one moiety having the structure:

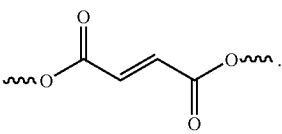

"Propargyl" as used herein, refers to a compound bearing at least one moiety having the structure:

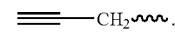

"Cyanate" as used herein, refers to a compound bearing at least one moiety having the structure:

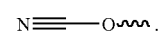

As used herein, "norbornyl" refers to a compound bearing at least one moiety having the structure:

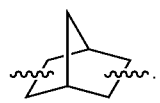

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

The term "solvent," as used herein, refers to a liquid that dissolves a solid, liquid, or gaseous solute, resulting in a solution. "Co-solvent" refers to a second, third, etc. solvent used with a primary solvent.

As used herein, "alcohol catalyst" refers to an alcohol or combination of alcohols that, when added to a chemical reaction, has the effect of accelerating, increasing the rate or yield of the reaction without being consumed by the overall reaction. Typically, an alcohol catalyst will contain a single alcohol, but mixtures comprising two or more alcohols are contemplated for use in the present invention.

As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

"Glass transition temperature" or "$T_g$": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

The "Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

"Thermogravimetric analysis" or "TGA" refers to a method of testing and analyzing a material to determine changes in weight of a sample that is being heated in relation to change in temperature. "Decomposition onset" refers to a temperature when the loss of weight in response to the increase of the temperature indicates that the sample is beginning to degrade.

The present invention provides novel linear or cyclic siloxane monomers useful in a variety of applications, such as adhesive applications. The general structure of the siloxane compounds of the invention may be illustrated by formula I:

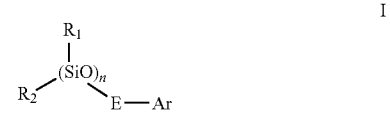

where $R_1$ is a $C_1$ to $C_{10}$ alkyl, $R_2$ is absent (for cyclic siloxanes) or is a $C_1$ to $C_{10}$ alkyl (for linear siloxanes), E is an alkenylene or oxiranylene, Ar is a substituted or an unsubstituted aryl, and n is an integer between 1 and 20. Compounds of the present invention, according to some embodiments, contain less than about 25 mass % of oxygen.

In some embodiments, each of $R_1$ and $R_2$ (if present) is a $C_1$ to about $C_5$ alkyl, such as a $C_1$ to about $C_3$ alkyl, such as methyl. In other embodiments, each of $R_1$ and $R_2$ (if present) is a $C_2$ to about $C_{10}$ alkyl, or a $C_5$ to about $C_{10}$ alkyl.

In certain embodiments, E is a $C_2$ alkenylene to about $C_{20}$ alkenylene, for example an alkenylene having at least about 3-10 carbon atoms. In some embodiments, Ar is a substituted or an unsubstituted $C_6$ aryl. In some aspects, E is a $C_2$ alkenylene and Ar is a substituted or and unsubstituted $C_6$ aryl. In some embodiments, E is $C_2$ oxiranylene and Ar is a substituted or an unsubstituted $C_6$ aryl.

If Ar that is used is a substituted aryl, it may include at least one substituent selected such as an alkyl, an alkenyl, an alkynyl, hydroxy, oxo, an alkoxy, mercapto, an unsubstituted cycloalkyl, a substituted cycloalkyl, an unsubstituted heterocyclic moiety, a substituted heterocyclic moiety, an unsubstituted aryl, a substituted aryl, an unsubstituted heteroaryl, a substituted heteroaryl, an unsubstituted aryloxy, a substituted aryloxy, a halogen, a haloalkyl, cyano, nitro, nitrone, amino, amido, —C(O)H, —C(O)—, —OC(O)—, —(O)CO—, —S—, —S(O)$_2$—, —OC(O)—O—, —NR—C(O)—, —NR—C(O)—NR—, —OC(O)—NR—, wherein R' is H, a lower alkyl, an acyl, an oxyacyl, carboxyl, carbamate, sulfonyl, sulfonamide, or sulfuryl.

In certain embodiments, n is 1-10, 2 to 15 or 4-20. In certain other embodiments, n is 3 to 6.

For linear siloxanes encompassed by the general structure I, both the substituents $R_1$ and $R_2$ are present, and the general structure of such linear siloxanes is represented by formula II:

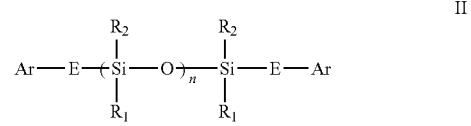

wherein each of $R_1$ and $R_2$ is independently an $C_1$ to $C_{10}$ alkyl, and the meanings for Ar, E, and n are the same as above.

In one aspect, the siloxane compounds of formula I and/or II can be used as Diels-Alder type curatives for bismaleimide or poly-maleimide monomers. Exemplary, non-limiting compounds according to formula I include compounds 1-3 as follows:

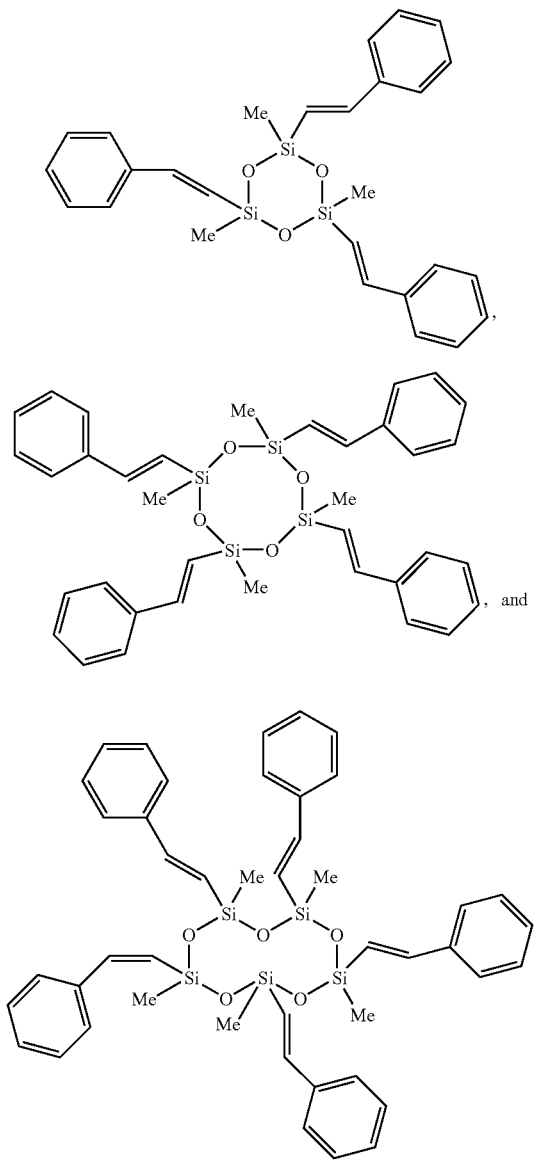

A non-limiting, exemplary compound according to formula II is compound 4:

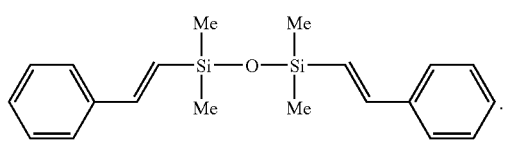

The exemplary invention siloxane compounds depicted above can act as co-monomers in thermoset compositions with a bismaleimide or poly-maleimide compounds. Therefore, these compounds will be effective Diels-Alder curatives for bis- and poly-maleimide resins.

The unsaturated siloxane monomers according to formula I and II also offer advantageous properties for use as maleimide curatives due to their poly-functionality. Each substituted styrenyl reside can react with two maleimide functional groups. Thus, an invention adhesive composition typically contains an excess of bismaleimide monomers.

In a further embodiment of the invention, the above-described unsaturated, siloxane and cyclic siloxane compounds can be converted to the corresponding epoxies, as exemplified below by compounds 5-8:

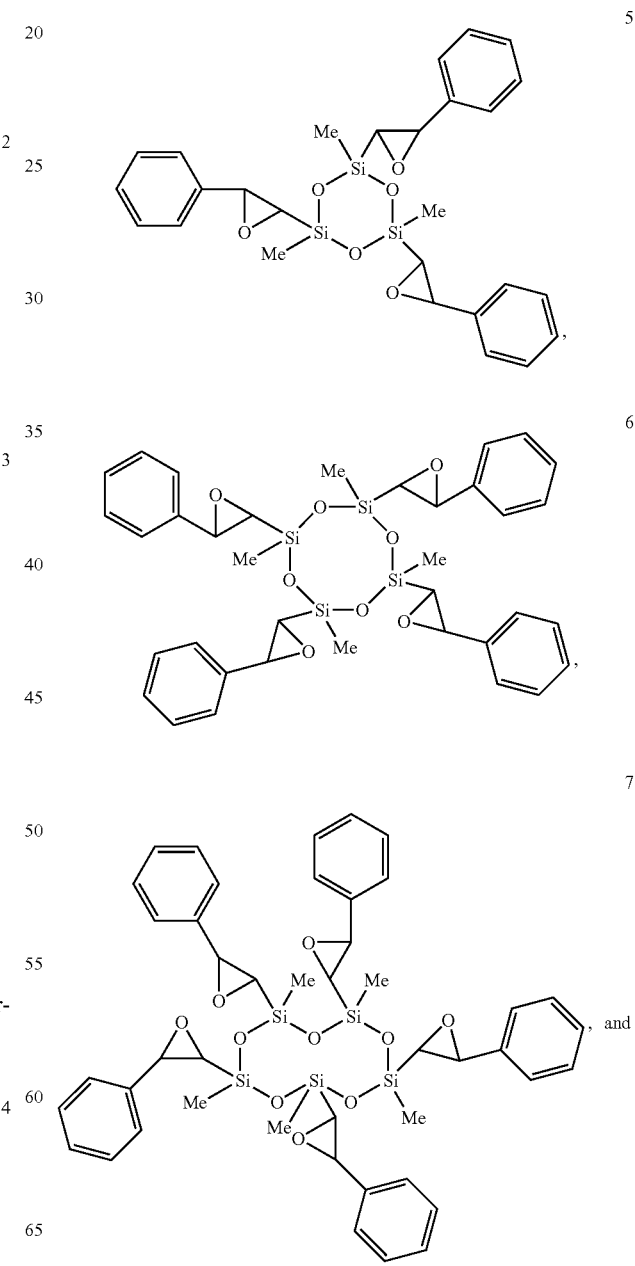

-continued

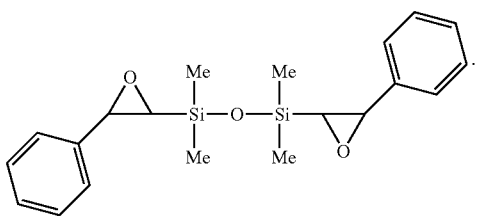

The resulting epoxies are notable for their low viscosities, high glass transition temperatures, excellent hydrolytic stability, low dielectric constants, and low ionic and total chloride content. As such, these compounds make ideal base resins for use in electronic materials applications.

The unsaturated compounds of this invention are prepared via hydrosilylation of phenylacetylene and linear or cyclic alkylhydrosiloxane. This hydrosilylation reaction is usually catalyzed via the addition of precious metal catalysts. These catalysts include platinum on carbon, platinum-divinyltetramethyldisiloxane complex, chloroplatinic acid, and organo-soluble rhodium salts. The hydrosilylation reactions are usually conducted at a temperature between 80 and 110° C.

The epoxy compounds of this invention can be prepared via a variety of epoxidation procedures that are well known to those in the art. Epoxidation of the olefin compounds can be accomplished via reaction with a peracid such as peracetic acid, perbenzoic acid, or m-chloroperbenzoic acid. Epoxidation can also be accomplished via oxidation of the parent olefin using hydrogen peroxide and alkaline or alkaline earth salts tungstic acid in the presence of a phase transfer catalyst.

The compounds of the present invention are useful in a variety of other applications. Invention compounds can be used in automotive, marine, and aerospace coatings and adhesives. The properties of certain invention compounds make these compounds suitable for use in dental matrix resins and adhesives. Invention compounds can also be used as components of matrix resins for composites used in sports equipment, automotive bodies, and boat construction. The compounds of this invention also have attractive properties for use in adhesives for diverse industrial applications such as threadlock materials and building materials.

Compositions Containing Siloxane Monomers

The present invention provides compositions containing at least one siloxane compound according to formula I or II, above. For example, the siloxane compound may be used independently as an adhesive or may be combined with other materials and reagents to prepare adhesive compositions. In certain embodiments, the siloxane compound may be combined with other adhesives and/or resins to prepare adhesive compositions. A siloxane compound of the invention may be used as the sole monomer of an adhesive composition of the invention. In other embodiments, the siloxane compound of the invention may be combined with other monomers, such as thermoset monomers, to make a fully formulated adhesive composition.

In certain embodiments of the invention, a siloxane compound according to formula I or II is present in a composition, such as an adhesive composition, in an amount from 0.5 weight percent (wt %) to about 98 wt %, based on the total weight of the composition. Typically, the composition will contain an amount of the siloxane compound equal to at least about 5 wt %, often at least about 10 wt %, frequently at least about 20 wt %, and in some embodiments at least about 40 wt % based on the total weight of the composition.

In another embodiment of the invention, the composition containing the siloxane compound of formula I and/or II includes at least one co-monomer, which is typically present in an amount from 10 wt % to about 90 wt %, based on the total weight of the composition. In some aspects of the invention, the composition will contain an amount of the co-monomer equal to at least about 15 wt %, often at least about 20 wt %, frequently at least about 25 wt %, and in some embodiments at least about 30 wt % based on the total weight of the composition. Co-monomers suitable for use in the siloxane monomer-containing compositions according to the invention include, but are not limited to, acrylates, acrylamides, methacrylates, methacrylamides, cyanate esters, maleimides, vinyl ethers, vinyl esters, styrenic compounds, allyl functional compounds, and olefins.

Curing Initiators. In certain embodiments, the present invention provides compositions, such as adhesive compositions, including at least one siloxane compound of formula I and/or II and at least one curing initiator. The curing initiator is typically present in adhesive compositions of the invention at an amount from 0.1 wt % to about 5 wt %, based on total weight of the composition, and is typically a free-radical initiator. In some embodiments, the curing initiator is present at least about 0.5 wt %, often at least about 1 wt %, frequently at least about 2 wt %, at in some embodiments at least about 3 wt %, based on total weight of the composition.

Free-radical initiators contemplated for use in the practice of the present invention typically decompose (i.e., have a half life in the range of about 10 hours) at temperatures in the range of about 70° C. up to 180° C. Exemplary free radical initiators contemplated for use in the practice of the present invention include peroxides (e.g. dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)). Other free-radical initiators that will be well-known in the art may also be suitable for use in the compositions of the present invention.

Photoinitiators. Free radical initiators also include photoinitiators. For invention compositions that contain a photoinitiator, the curing process can be initiated, for example, by UV radiation. In one embodiment, the photoinitiator is present at a concentration of 0.1 wt % to 5 wt %, based on the total weight of the organic compounds in the composition (excluding any filler). In one embodiment, the photoinitiator comprises 0.5 wt % to 3.0 wt %, based on the total weight of the organic compounds in the composition. In other embodiments, the photoinitiator is present at least about 0.5 wt %, often at least about 1 wt %, frequently at least about 2 wt %, and in some embodiments at least about 3 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive compositions of the invention.

In certain embodiments, the invention provides adhesive compositions including 0.5 wt % to about 98 wt % of at least one siloxane compound described herein, based on total weight of the composition; optionally, 10 wt % o about 90 wt % of at least one co-monomer selected from acrylates, methacrylates, maleimides, vinyl ethers, vinyl esters, styrenic compounds, allyl functional compounds, and olefins, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Additional Co-Curing Compounds. In certain aspects, the adhesive compositions of the invention include at least one additional compound that can co-cure with the siloxane compound of formula I. The additional compound is typically present in the adhesive compositions from about 10 wt % to about 90 wt % based on total weight of the composition. In such aspects, the composition will typically contain an amount of the co-curing compound equal to at least about 20 wt %, often at least about 30 wt %, frequently at least about 40 wt %, and in some embodiments at least about 50 wt % based on the total weight of the composition. Such compounds include, for example, epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional mono-maleimides, bismaleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof.

Coupling Agents. In certain aspects, the adhesive compositions of the invention include at least one additional coupling agent. Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

Adhesive Paste Compositions Containing Siloxane Compound

In certain embodiments, the present invention provides adhesive compositions that are of various consistencies including, liquids, gels, pastes and solids. In one embodiment, the adhesive composition is a paste suitable for attaching an electronics die to a substrate (i.e., die-attach pastes). Die attach pastes of the invention are optimized for long-term reliability, rapid inline curing, long pot-life, viscosity and thixotropic control for fast automated dispensing and manufacturing.

In one embodiment, the present invention provides an adhesive composition that include 0.5 wt % to about 98 wt % based on total weight of the composition, of a compound represented by structural formula I; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

B-Stageable Adhesives

In certain embodiments, the adhesive compositions and die attach pastes of the invention are b-stageable. As used herein, "B-stageable" refers to the properties of an adhesive having a first solid phase followed by a tacky rubbery stage at elevated temperature, followed by yet another solid phase at an even higher temperature. The transition from the rubbery stage to the second solid phase is thermosetting. However, prior to that, the thermosetting material behaves similarly to a thermoplastic material. Thus, such adhesives allow for low lamination temperatures while providing high thermal stability.

The B-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this B-staged adhesive in a final heating step to bond two or more parts together. Thus, this dual stage cure method of the invention is particularly advantageous for silicon wafer back coatings. The original adhesive mixture can be spin coated onto the back of a silicon wafer. The coating can then be B-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the B-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the B-stageable adhesive is spin-coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the B-stageable adhesive have slopes ranging from 1.0 to about 1.2.

In some instances, the B-stageable adhesive is dispensed onto the backside of a die that has been coated with a polyimide. Thus, the solvent or solvent system used to dispense the B-stageable adhesive should not have any deleterious effects on the polyimide coating. To achieve this goal, in certain embodiments, the solvent system will include a polar solvent in combination with a nonpolar solvent. Typically, the polar solvent is suitable for use with the siloxane compounds described herein in B-stageable adhesives, and the nonpolar solvent is a non-solvent for the siloxane compounds. In addition, the polar solvent typically has a lower boiling point than the non-polar solvent. Without wishing to be to be limited to a particular theory, it is believed that when the adhesive is dispensed and then B-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, adhesive compositions such as die-attach pastes and B-stageable adhesive compositions of the invention, will cure within a temperature range of 80-220° C., and curing will be effected within a length of time of less than 1 minute up to about 60 minutes. The B-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to a particular industrial manufacturing process.

Additional Compounds. In certain embodiments, the compositions of the invention, such as adhesives (including die-attach paste adhesives), may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be present in an amount up to about 15 percent by weight of siloxane monomer according formula I and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine.

Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives. Commercially acceptable values for die shear for the adhesives on a 80×80 mil$^2$ silicon die are in the range of greater than or equal to 1 kg at room temperature, and greater than or equal to 0.5 kg at 260° C. Acceptable values for warpage for a 500×500 mil$^2$ die are in the range of less than or equal to 70 Nm at room temperature.

Fillers. In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, zinc oxide, alumina, and the like. Compounds which act primarily to modify rheology include polysiloxanes (such as polydimethyl siloxanes), silica, fumed silica, fumed alumina, fumed titanium dioxide, calcium carbonate and the like.

Underfill Compositions

During its normal service life, an electronic assembly is subjected to repeated cycles of widely varying temperature. Due to the differences in the coefficient of thermal expansion between the electronic component, the solder, and the substrate, thermal cycling can stress the components of the assembly and cause it to fail. To prevent the failure, the gap between the component and the substrate is filled with an underfill material to reinforce the solder material and to absorb some of the stress of the thermal cycling.

In practice, the underfill material is typically dispensed into the gap between and electronic component (such as a flip-chip) and the substrate by injecting the underfill along two or more sides of the component, with the underfill material flowing, usually by capillary action, to fill the gap. Alternatively, underfilling can be accomplished by backfilling the gap between the electronic component and the substrate through a hole in the substrate beneath the chip. In either method, the underfill material must be sufficiently fluid to permit filling very small gaps.

The requirements and preferences for underfills are well known in the art. Specifically, monomers for use in underfills should have high $T_g$ and low $\alpha_1$ CTE, important properties. A high $T_g$, preferably in the range of at least about 100-135° C., and a low $\alpha_1$ preferably lower than about 60-65 ppm/° C., are optimal for underfill compositions.

The siloxanes compounds of the invention are particularly suited as monomers or co-monomers in underfill compositions. Thus, the present invention provides underfill compositions including at least one compound according to formula I or formula II. Optionally, the underfill will also contain a fluxing agent and/or a filler.

Two prominent uses for underfill technology are in packages known in the industry as flip-chip, in which a chip is attached to a lead frame, and ball grid array, in which a package of one or more chips is attached to a printed wire board.

The underfill encapsulation may take place after the reflow of the metallic or polymeric interconnect, or it may take place simultaneously with the reflow. If underfill encapsulation takes place after reflow of the interconnect, a measured amount of underfill encapsulant material will be dispensed along one or more peripheral sides of the electronic assembly and capillary action within the component-to-substrate gap draws the material inward. The substrate may be preheated if needed to achieve the desired level of encapsulant viscosity for the optimum capillary action. After the gap is filled, additional underfill encapsulant may be dispensed along the complete assembly periphery to help reduce stress concentrations and prolong the fatigue life of the assembled structure. The underfill encapsulant is subsequently cured to reach its optimized final properties.

If underfill encapsulation is to take place simultaneously with reflow of the solder or polymeric interconnects, the underfill encapsulant, which can include a fluxing agent if solder is the interconnect material, first is applied to either the substrate or the component; then terminals on the component and substrate are aligned and contacted and the assembly heated to reflow the metallic or polymeric interconnect material. During this heating process, curing of the underfill encapsulant occurs simultaneously with reflow of the metallic or polymeric interconnect material.

A wide variety of acids are contemplated for use as the acidic fluxing agent. Typically, the acidic fluxing agent is a carboxylic acid such as, for example, 3-cyclohexene-1-carboxylic acid, 2-hexeneoic acid, 3-hexeneoic acid, 4-hexeneoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristolic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid, oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, meso-2,3-dimethylsuccinic acid, glutaric acid, (+/−)-2-methylglutaric acid, 3-methylglutaric acid, 2,2-dimethylglutaric acid, 2,4-dimethylglutaric acid, 3,3-dimethylglutaric acid, adipic acid, 3-methyladipic acid, (R)-(+)-3-methyladipic acid, 2,2,5,5-tetramethylhexanedioic acid, pimelic acid, suberic acid, azelaic acid, 1,10-decanedicarboxylic acid, sebacic acid, 1,11-undecanedicarboxylic acid, undecanedioic acid, 1,12-dodecanedicarboxylic acid, hexadecanedioic acid, docosanedioic acid, tetracosanedioic acid, tricarballylic acid, beta-methyltricarballylic acid, 1,2,3,4-butanetetracarboxylic acid, itaconic acid, maleic acid, fumaric acid, citraconic acid, mesaconic acid, trans-glutatonic acid, trans-beta-hydromuconic acid, trans-traumatic acid, trans, trans-muconic acid, cis-aconitic acid, trans aconitic acid, (+/−)-chlorosuccinic acid, (+/−)-bromosuccinic acid, meso-2,3-dibromosuccinic acid, hexa fluoroglutaric acid, perfluoroadipic acid hydrate, dibromo-maleic acid, DL-malic acid, D-malic acid, L-malic acid, (R)-(−)-citramalic acid, (S)-(+)-citramalic acid, (+/−)-2-isopropylmalic acid, 3-hydroxy-3-methylglutaric acid, ketomalonic acid monohydrate, DL-tartaric acid, L-tartaric acid, D-tartaric acid, mucic acid, citric acid, citric acid monohydrate, dihydroflumaric acid hydrate, tetrahydrofuran-2,3,4,5-tetracarboxylic acid, mercaptosuccinic acid, meso-2,3-dimercaptosuccinic acid, thiodiglycolic acid, 3,3'-thiodipropionic acid, 3,3'-dithiodipropionic acid, 3-carboxypropyl disulfide, (+/−)-2-(carboxymethylthio) succinic acid, 2,2',2",2"'-[1,2-ethanediylidenetetrakis(thio)]-tetrakisacetic acid, nitromethanetrispropionic acid, oxalacetic acid, 2-ketoglutaric acid, 2-oxoadipic acid hydrate, 1,3-acetonedicarboxylic acid, 3-oxoadipic acid, 4-ketopimelic acid, 5-oxoazelaic acid, chelidonic acid, 1,1-cyclopropanedicarboxylic acid, 1,1-cyclobutanedicarboxylic acid, (+/−)-trans-1,2-cyclobutanedicarboxylic acid, trans-DL-1,2-cyclopentanedicarboxylic acid, 3,3-tetramethyleneglutaric acid, (1R.3S)-(+)-camphoric acid, (1S.3R)-(−)-camphoric acid, (+/−)-cyclohexylsuccinic acid, 1,1-cyclohexanediacetic acid, (+/−)-trans-1,2-cyclohexanedicarboxylic acid, (+/−)-1,3-cyclohexanedicarboxylic acid, trans-1,2-cyclohexanedicarboxylic acid, 1,4-cyclohexanedicarboxylic acid, 1,3-adamantanedicarboxylic acid, 3-methylenecyclopropane-trans-1,2-dicarboxylic acid, cis-5-norbornene-endo-2,3-dicarboxylic acid, 1,3,5-cyclohexanetricarboxylic acid, 1,3,5-cyclohexanetricarboxylic acid, kemp's triacid, (1alpha.3alpha.5beta)-1,3,5-trimethyl-1,3,5-cyclohexanetricarboxylic acid, 1,2,3,4-cyclobutane-tetracarboxylic acid, and 1,2,3,4,5,6-cyclo-hexanehexacarboxylic acid monohydrate, phenylmalonic acid, benzylmalonic acid, phenylsuccinic acid, 3-phenylglutaric acid, 1,2-phenylenediacetic acid, homophthalic acid, 1,3-phenylenediacetic acid, 4-carboxyphenoxyacetic acid, 1,4-phenylenediacetic acid, 2,5-dihydroxy-1,4-benzenediacetic acid, 1,4-phenylenediacrylic acid, phthalic acid, isophthalic acid, 1,2,3-benzenetricarboxylic acid hydrate, terephthalic acid, 1,2,4-benzenetricarboxylic acid, 1,2,4,5-benzenetetracarboxylic acid, mellitic acid, 3-(carboxymethylaminomethyl)-4-hydroxybenzoic acid, 4-methylphthalic acid, 2-bromoterephthalic acid, 4-bromoisophthalic acid, 4-hydroxyisophthalic acid, 4-nitrophthalic acid, nitrophthalic acid, 1,4-phenylenedipropionic acid, 5-tert-butylisophthalic acid, 5-hydroxyisophthalic acid, 5-nitroisophthalic acid, 5-(4-carboxy-2-nitrophenoxy)-isophthalic acid, diphenic acid, 4,4'-biphenyldicarboxylic acid, 5,5'dithiobis(2-nitrobenzoic acid), 4-[4-(2-carboxybenozoyl)phenyl]-butyric acid, pamoic acid, 1,4-naphthalenedicarboxylic acid, 2,3-naphthalenedicarboxylic acid, 2,6-naphthalenedicarboxylic acid, 1,4,5,8-naphthalene-tetracarboxylic acid hydrate, 2,7-di-tert-butyl-9,9-dimethyl-4,5-xanthenedicarboxylic acid, and the like.

A particularly useful carboxylic acid for the preparation of the latent fluxing agents of the present invention is DIACID 1550®, a monocyclic $C_{21}$ dicarboxylic acid product derived from tall oil fatty acids, commercially available from Westvaco Corporation.

Mold Compounds and Compositions

In the electronics industry, a semiconductor chip or die mounted to a "package" substrate may be overmolded with a mold compound to provide a level of protection from environmental effects such as moisture and contaminants.

In terms of reliability performance, various properties of mold compositions materials are generally considered important. The properties desirable for mold compositions are known in the art. See, for example, U.S. Pat. Nos. 7,294,915, 6,512,031, and 6,429,238. These include low CTE, low modulus, adhesion, and high fracture toughness of the cured resin. A high $T_g$, preferably in the range of at least about 100-135° C., and a low modulus or $\alpha_1$, preferably lower than about 60-65 ppm/° C., are optimal for mold compositions. See, for example, U.S. Pat. Nos. 6,512,031 and 5,834,848. A typical overmolding process places a solid or semi-solid molding compound over the chip using a mold press. The package is then transferred through a heated mold that causes the molding compound to flow and encapsulate the chip.

Mold compositions are highly filled compositions. They are typically filled with silica. This high filler loading is critical to their performance in terms of CTE (coefficient of thermal expansion), flame retardance, and thermal conductivity.

The compounds of the present invention were found to have properties desirable of mold compounds. Specifically, the siloxanes monomers of the invention have a high $T_g$ and low $\alpha_1$ CTE. A high $T_g$, preferably in the range of at least about 100-135° C., and a low modulus or $\alpha_1$, preferably lower than about 60-65 ppm/° C., are optimal for mold compositions. Thus, the present invention provides mold compositions containing at least one compound according to formula I or II.

Assemblies

The present invention also provides assemblies of components adhered together by the above-described adhesive compositions (e.g., B-stageable adhesives and die-attach pastes) of the invention. Thus, for example, assemblies comprising a first article adhered to a second article by a cured aliquot of an adhesive composition containing at least one compound of formula I are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions.

Additional embodiments of the invention include adhesively bonded structures containing at least one siloxane compound described herein. Non-limiting examples of the adhesively bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

Methods of Using Siloxane Monomer Compounds and Adhesive Compositions

According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this method, the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin-coating, spray coating, stencil printing, screen printing and other methods well known in the art.

It will be understood those of skill in the art that using the compounds and methods of the present invention, it is possible to prepare adhesives having a wide range of cross-link density by the judicious choice and amount of a compound have a structure represented by formula I. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

In still further embodiments, the invention provides B-stageable type methods for adhesively attaching a semiconductor die to a substrate. Such methods can be performed, for example, by applying an invention adhesive composition to the substrate, the semiconductor device or both the substrate and the semiconductor device; melting the applied adhesive composition applied; (c) contacting the semiconductor device and the substrate, such that the die and substrate are separated only by the applied adhesive composition; and curing the applied adhesive composition, thereby attaching the semiconductor device to the substrate.

Properties of Adhesives Containing Siloxane Monomers

Advantageously, the siloxanes monomers of the invention can impart many properties that are desirable in an adhesive. Historically, the large majority of integrated circuits have been mounted on printed circuit boards using lead-based soldering. However, the demand for lead-free materials is increasing year by year, and electrically conductive adhesives are seen as an environmentally-friendly alternative.

Adhesiveness. To fully replace lead-based solders, adhesives in the microelectronic industry, adhesives must address the need for signal and power distribution, heat dissipation (i.e., cooling) while at the same time having and maintaining high adhesiveness. Conductive adhesives, for example, typically have conductive fillers dispersed in a polymer matrix. The polymer matrix, when cured, provides the mechanical adhesion, but can interfere with conductivity and increase electrical resistance.

Compounds of the present invention can be used to increase adhesiveness of polymer compositions. When added to a BMI-containing adhesive compositions, siloxane compounds of the invention increased adhesiveness by nearly two-fold over the same composition containing only BMI, as illustrated in EXAMPLE 2, below.

Thus the present invention provides methods for increasing the adhesiveness of an adhesive composition by replacing all or a portion of a monomer (such as an acrylate or maleimide monomer) in the composition, with a siloxane compound of the invention. In one embodiment, the siloxane compound can be represented by structural formula I. In other embodiments the siloxane compound can be represented by structural formula II.

The invention will now be further described with reference to the following non-limiting examples.

EXAMPLES

Example 1

A 125 ml flask was charged with 3.5 g (0.026 mole) 1,1,3,3-tetramethyldisiloxane, 5.5 g (0.054 mole) phenylacetylene, and 25 ml toluene. A crystal of chloroplatinic acid was then added. This mix was stirred magnetically and heated at 100° C. for two hours. Fourier transform infrared spectroscopy (FTIR) of the product in the flask indicated that the hydrosilation reaction was complete (the ethynyl C—H stretch at 3297 wavenumbers and the Si—H absorption at 2130 wavenumbers were both gone). The solution was passed over five grams of silica gel in a fritted funnel. The silica gel was then rinsed with another 25 ml of fresh toluene. The toluene and excess phenylacetylene were then removed via rotary evaporation and air sparge to yield 8.5 g (97% of theory) of a clear, yellow liquid. The product had prominent infrared absorptions at 1252, 1044, 842, and 688 wavenumbers. A TGA was run on the product which revealed no weight loss at 100° C., and an onset (evaporation) at 216° C.

Example 2

A mixture was made containing fifty equivalent percent of the monomer from EXAMPLE 1 in the bismaleimide of the dimer diamine (X-BMI; which was prepared as described in the U.S. Pat. No. 5,973,166, the entire disclosure of which is incorporated herein by reference. X-BMI is a product which is described in U.S. Pat. No. 5,973,166, EXAMPLE 6, the fourth product in Table 1. As can be understood from the description provided in U.S. Pat. No. 5,973,166, X-BMI is a bismaleimide of Versamine® 552, prepared by using methanesulfonic acid and triethylamine). This mixture was tested with and without 2% added dicumyl peroxide catalyst. The catalyst-free mix had a broad exotherm starting at 148° C. and achieved a maximum at 252° C. The catalyzed mix had an onset at 155° C., a maxima at 175° C. and a cure energy of 274.9 joules per gram. A control, consisting of only the X-BMI and the same catalyst, had a cure maximum at 147° C. and a cure energy of 242 joules per gram.

The two dicumyl peroxide catalyzed mixtures (i.e. the one containing 50 equivalent percent of the monomer from EXAMPLE 1 in X-BMI, and the X-BMI only control) were used to bond aluminum (0.177 inch diameter) studs to freshly cleaned copper slugs. Room temperature adhesion data was generated for these samples using a Sebastian III tensile tester. The results of those tests are summarized in Table 1.

TABLE 1

Tensile Adhesion for Siloxane + X-BMI Versus All X-BMI Control

| 1:1 Equivalents of Monomer of Example 1 and X-BMI (with 2% DICUP, cured 1.0 hr @ 200° C.) | | X-BMI-Only Control (with 2% DICUP, cured 1.0 hr @ 200° C.) | |
| --- | --- | --- | --- |
| Part | Adhesion (lbs. force) | Part | Adhesion (lbs. force) |
| 1 | 55 | 1 | 40 |
| 2 | 26 | 2 | 24 |
| 3 | 74 | 3 | 11 |
| 4 | 56 | 4 | 29 |
| 5 | 59 | 5 | 44 |
| 6 | 69 | 6 | 25 |
| 7 | 41 | 7 | 31 |
| 8 | 63 | 8 | 9 |
| 9 | 29 | 9 | 30 |
| 10 | 59 | 10 | 38 |
| Average = 53.1 lbs Std. dev. = 16.1 lbs | | Average = 28.1 lbs. Std. dev. = 11.5 lbs. | |

The adhesion of the test mixture was nearly twice that of the control.

While this invention has been described with respect to these specific examples, it should be clear that other modifications and variations would be possible without departing from the spirit of this invention.

What is claimed is:

1. A cyclic or linear siloxane compound having the structure of formula I:

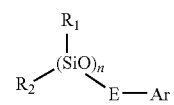

wherein:
$R_1$ is selected from the group consisting of $C_1$ to $C_{10}$ alkyls;
$R_2$ is absent or is selected from the group consisting of $C_1$ to $C_{10}$ alkyls;
E is an oxiranylene;
Ar is a substituted or an unsubstituted phenyl; and
n is an integer having the value between 1 and 20.

2. The compound of claim 1, wherein the compound is a cyclic siloxane, $R_2$ is absent, and n has the value between 3 and 6.

3. The compound of claim 2, wherein $R_1$ is selected from the group consisting of $C_1$ to about $C_{10}$ alkyls.

4. The compound of claim 2, wherein $R_1$ is methyl.

5. The compound of claim 2, wherein E is $C_2$ alkenylene.

6. The compound of claim 2, wherein the substituted phenyl comprises at least one substituent selected from the group consisting of an alkyl, an alkenyl, an alkynyl, hydroxy, an alkoxy, mercapto, an unsubstituted cycloalkyl, a substituted cycloalkyl, an unsubstituted heterocyclic moiety, a substituted heterocyclic moiety, an unsubstituted aryl, a substituted aryl, an unsubstituted heteroaryl, a substituted heteroaryl, an unsubstituted aryloxy, a substituted aryloxy, a halogen, a haloalkyl, cyano, nitro, nitrone, amino, amido, —C(O)H, —C(O)—, —OC(O)—, —(O)CO—, —S—, —S(O)$_2$—, —OC(O)—O—, —NR'—C(O)—, —NR'—C(O)—NR'—, and —OC(O)—NR'—, wherein R' is selected from the group consisting of H, a lower alkyl, an acyl, an oxyacyl, carboxyl, carbamate, sulfonyl, sulfonamide, and sulfuryl.

7. A composition comprising a compound of claim 1, wherein the composition is selected from the group consisting of an adhesive and a coating.

8. The composition of claim 7, wherein the composition is an underfill adhesive.

9. The composition of claim 8, further comprising at least one of a fluxing agent and a filler.

10. A compound of claim 1, wherein the compound is a linear siloxane having the structure of formula II:

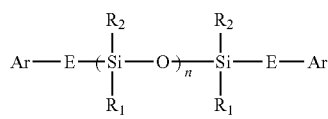

wherein each $R_2$ is independently selected from the group consisting of $C_1$ to $C_{10}$ alkyls.

11. A compound having the structure 4:

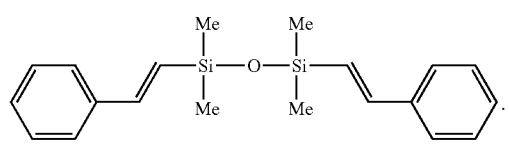

12. A compound of claim 1, selected from the group consisting of compounds 5, 6, 7, and 8:

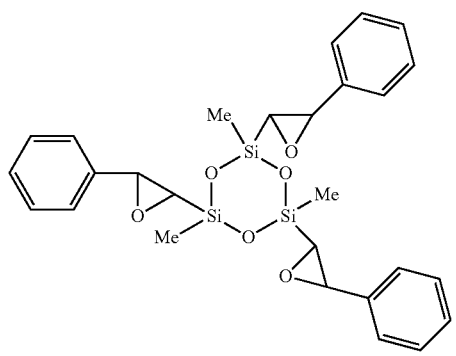

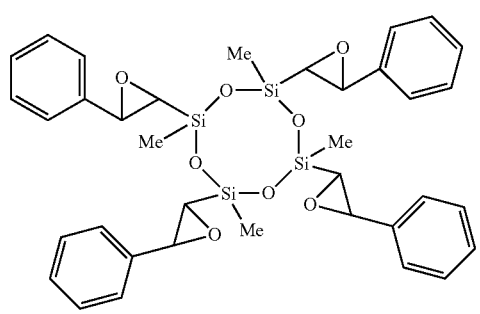

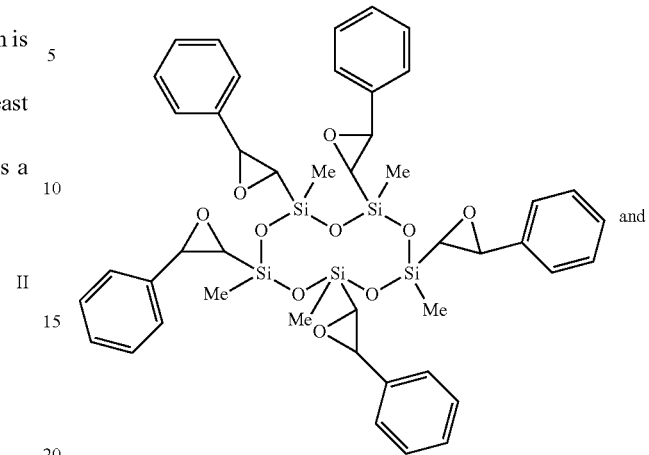

13. A method for increasing the adhesiveness of a composition comprising a monomer by replacing all or a portion of the monomer in the composition with a compound of claim 1.

14. A cyclic or linear siloxane compound having the structure of formula I:

$$R_2 \overset{R_1}{\underset{}{\diagup}} (SiO)_n \diagdown E-Ar$$

I wherein:
$R_1$ is selected from the group consisting of $C_1$ to $C_{10}$ alkyls;
$R_2$ is absent or is selected from the group consisting of $C_1$ to $C_{10}$ alkyls;
E is an alkenylene;
Ar is a substituted phenyl comprising at least one substituent selected from the group consisting of an alkenyl, an alkynyl, hydroxy, mercapto, an unsubstituted cycloalkyl, a substituted cycloalkyl, an unsubstituted heterocyclic moiety, a substituted heterocyclic moiety, an unsubstituted aryl, a substituted aryl, an unsubstituted heteroaryl, a substituted heteroaryl, an unsubstituted aryloxy, a substituted aryloxy, a haloalkyl, cyano, nitrone, amido, —C(O)H, —C(O)—, —OC(O)—, —(O)CO—, —S—, —S(O)$_2$—, —OC(O)—O—, —NR'—C(O)—, —NR'—C(O)—NR'—, and —OC(O)—NR'—, wherein R' is selected from the group consisting of H, a lower alkyl, an acyl, an oxyacyl, carboxyl, carbamate, sulfonyl, sulfonamide, and sulfuryl; and n is an integer having the value between 1 and 20.

15. The compound of claim 14, wherein the compound is a cyclic siloxane, $R_2$ is absent, and n has the value between 3 and 6.

16. The compound of claim 14, wherein $R_1$ is selected from the group consisting of $C_1$ to $C_{10}$ alkyls.

17. A composition comprising a compound of claim 14, wherein the composition is selected from the group consisting of an adhesive and a coating.

18. The composition of claim 17, further comprising at least one co-monomer selected from the group consisting of an acrylate, a methacrylate, a maleimide, a vinyl ether, a vinyl ester, styrenics and an allyl functional compound.

19. A method for increasing the adhesiveness of a composition comprising a monomer by replacing all or a portion of the monomer in the composition with a compound of claim 14.

* * * * *